CATHETER PLACEMENT UNIT

Original Filed June 8, 1966 2 Sheets-Sheet 1

INVENTOR.
JAMES L. SORENSON

BY Hill, Sherman, Meroni, Gross & Simpson ATTORNEYS

CATHETER PLACEMENT UNIT

Original Filed June 8, 1966 2 Sheets-Sheet 2

INVENTOR.
JAMES L. SORENSON

BY Hill, Sherman, Meroni, Gross & Simpson ATTORNEYS

United States Patent Office

Re. 27,797
Reissued Oct. 30, 1973

27,797

CATHETER PLACEMENT UNIT

James L. Sorenson, Salt Lake City, Utah, and Wallace H. Ring, P.O. Box 1133, Salt Lake City, Utah; said Sorenson assignor to said Wallace H. Ring Original No. 3,463,152, dated Aug. 26, 1969, Ser. No. 556,194, June 8, 1966. Application for reissue Dec. 14, 1970, Ser. No. 97,627

Int. Cl. A61m *5/00*

U.S. Cl. 128—214.4 13 Claims

Matter enclosed in heavy brackets [ ] appears in the original patent but forms no part of this reissue specification; matter printed in italics indicates the additions made by reissue.

ABSTRACT OF THE DISCLOSURE

The combination of the catheter placement unit including a needle and a catheter telescopically associated therewith, and wherein the needle is retractable relatively to the catheter following puncture of a body lumen, and locking means to hold the needle in retracted position in such manner that the patient's body is effectively protected from contact of the needle point.

This invention or discovery relates to improvements in a catheter placement unit, and more particularly to a unit highly desirable for placing a small catheter in a surface vein where large quantities of infusion fluid are not necessarily needed in a minimum of time, although the placement unit will have other uses and purposes as will be apparent to one skilled in the art.

Catheter placement units heretofore made and suitable for the cannulation of surface veins frequently resulted in infiltration of infusion liquid into tissues adjacent to a vein, and such infiltration would likely occur in half the cases where a 24 hour infusion was indicated. Also, with formerly known catheter placement units, difficulty was frequently experienced in making a proper venipuncture; the bulk of the apparatus was mentally depressing to the patient; and the needle could not be retracted and locked in position relatively to the catheter.

With the foregoing in mind, it is an important object of the instant invention to provide a catheter placement unit wherein the catheter is connected to the source of infusion in a leakproof manner, whereby infusion liquid does not directly contact the inside of a hollow needle, and infiltration of infusion liquid into adjacent tissues is eliminated.

Another important object of this invention is the provision of a catheter placement unit highly desirable for use in connection with surface veins, and wherein the needle with which the venipuncture is made is retractable relatively to the catheter and locked in its retracted position with the point of the needle well protected.

Also an object of this invention is the provision of a catheter placement unit which is so constructed that the needle may be disposed almost parallel to a surface vein at the time of venipuncture, and the device being of a relatively small size without bulkiness that might create a psychological fear or distress in the patient's mind.

While some of the more salient features, characteristics and advantages of the instant invention have been above pointed out, others will become apparent from the following disclosures, taken in conjunction with the accompanying drawings, in which.

Figure 1:
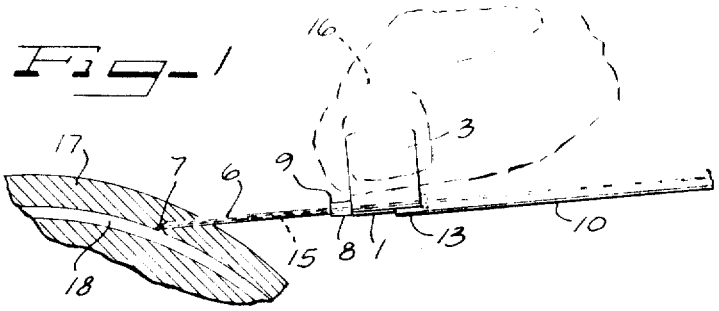
FIGURE 1 is a fragmentary part sectional part elevational view illustrating a catheter placement unit embodying principles of this invention in use.
Figure 2:
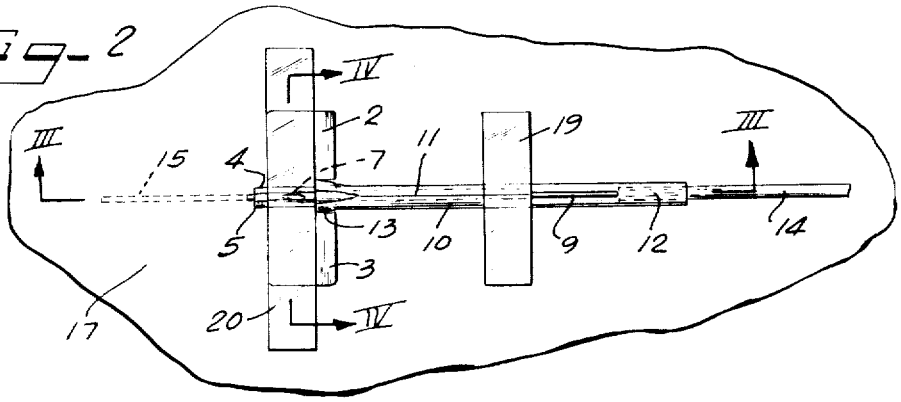
FIGURE 2 is a fragmentary plan view of the structure of FIGURE 1 after the catheter has been placed and the needle locked in a harmless position.
Figure 3:
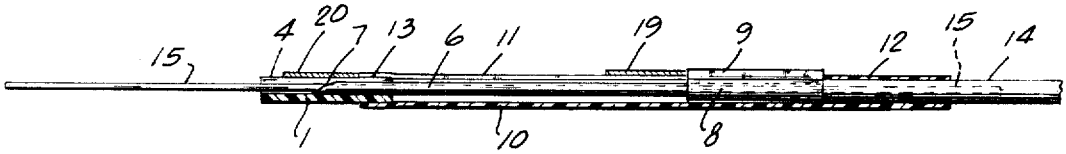
FIGURE 3 is an enlarged fragmentary vertical sectional view, taken substantially as indicated by the line III—III of FIGURE 2, looking in the direction of the arrows.
Figure 4:
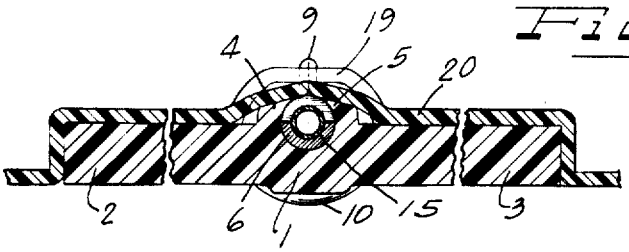
FIGURE 4 is a greatly enlarged fragmentary transverse vertical sectional view taken substantially as indicated by the line IV—IV of FIGURE 2.

All the illustrated embodiments of the instant invention have been shown exaggerated in size for purposes of clarity. Although the catheter placement units may be made in various sizes, for use with children or adults, and the catheters may be of various lengths depending upon what particular lumen of the body they are to be placed within, when utilized for cannulating surface veins, the placement units will be considerably smaller than illustrated.

With reference now to FIGURES 1 to 4 inclusive, it will be seen that the first illustrated embodiment of the instant invention includes a holding member 1 shaped to provide opposed side wings 2 and 3. This member may be formed of a suitable plastic material and is flexible although possessing far more rigidity than the catheter to be placed. Centrally thereof the member 1 is provided with a pair of spaced upstanding ribs 4 and 5 paralleling the longitudinal axis of the entire placement unit and defining a groove therebetween.

The placement unit also includes a hollow needle 6 having a pointed end 7 thereon to effect body puncture, and at the opposite end the needle is provided with a hub 8 with an upstanding flange 9 thereon. The hub 8 of the needle is slidable inside a plastic sheath 10 having a longitudinal slit 11 therein, the aforesaid flange 9 being of sufficient height to extend through the slit. The sheath may satisfactorily be extruded plastic, such as polyethylene, and is of sufficient resiliency that the slit normally remains closed. The slit terminates short of the outer end of the sheath, leaving a solid portion 12 of the sheath at the outer terminal end thereof. The other end of the sheath is secured to the holding member 1 adjacent the ribs 4 and 5 as seen at 13.

Secured within the closed end 12 of the sheath 10 is one end portion of a tube 14 which may be of plastic highly flexible material and which is of indefinite length, leading directly to a coupling with an infusion line depending from a bottle or other source of infusion liquid. This tube may be fused or adhesively connected to the sheath 10 as may be deemed most expedient. A catheter 15 extends through the sheath 10 and is disposed within the lumen of the needle 6, with one end terminating just inside the point of the needle and the other end fused or adhesively secured to the inside of the aforesaid infusion tube 14. The catheter is thus maintained sterile within the sheath 10 and the needle 6 until it is placed in the body of a patient.

At the outset, the placement unit is assembled with the needle hub disposed between the ribs 4 and 5 on the holding member 1, as seen in FIGURE 1. Of course there is the usual tubular protective cap disposed over the needle, which is not shown, and the entire unit is packaged in a sterile wrapper.

In use, the unit is extremely simple and effective. The sterile wrapper is opened, and the tube 14 connected to an infusion system. The needle cap is removed, and by grasping the flange 9 on the needle hub the needle is retracted just sufficiently to expose the end of the catheter. Infusion is then turned on and the catheter flushed out with infusion liquid to remove air and sterilization sediment, if any, from the catheter. The infusion is then turned off, and the needle advanced so the needle point is just beyond the end of the catheter. The flanges 2 and 3 of the holding member 1 are then bent upwardly and gripped between the thumb and finger of the attending surgeon as indicated at 16 in FIGURE 1. The upward bending of the flanges 2 and 3 causes the ribs 4 and 5 to tightly grip the needle hub so that there is no danger of slippage during venipuncture. The point of the needle is then inserted into the body 17 of a patient and then advanced to the desired extent into a vein 18, such as a vein on the back of the hand for example. Blood flowing backward through the needle and possibly into the catheter as well will be visible through the transparent sheath 10 to denote that a proper venipuncture has been made. After the needle has been advanced into the vein, the wings 2 and 3 are held flatly against the patient's body, and the needle is retracted by grasping the upstanding flange 9 and moved to the position seen in FIGURES 2 and 3 with the point 7 of the needle lying between the ribs 4 and 5, the catheter remaining extended in the lumen of the patient. The needle cannot be retracted too far because when the flange 9 contacts the closed end of the sheath at the end of the slit 11, the point of the needle will be properly disposed. A strip 19 of adhesive tape is then attached to the patient's body across the sheath 10 immediately adjacent the upstanding flange 9 on the needle hub as seen clearly in FIGURES 2 and 3, to lock the needle in its retracted position and prevent any forward movement of the needle thereafter which might result in injury to the catheter. A strip 20 of adhesive tape is also laid over the holding member 1, directly over the ribs 4 and 5 and the needle point to hold the entire unit securely on the patient's body with the catheter properly entered into the vein.

Two pieces of adhesive tape may be packaged along with the catheter unit so as to be immediately available and ready for use.

It will be noted that with the instant placement unit, the catheter is at all times sealed off from the needle in a leakproof manner, so that there cannot be any infiltration of infusion liquid into the body tissue adjacent the vein. There is no danger to the patient from the point of the retracted needle, nor any danger of injury to the catheter by virtue of unexpected forward movement of the needle, because the needle is securely locked in the retracted position and the point thereof well covered. Also, the device lies flatly on the patient's body, without any objectionable bulk that might cause a psychological reaction in the patient's mind.

Figure 5:
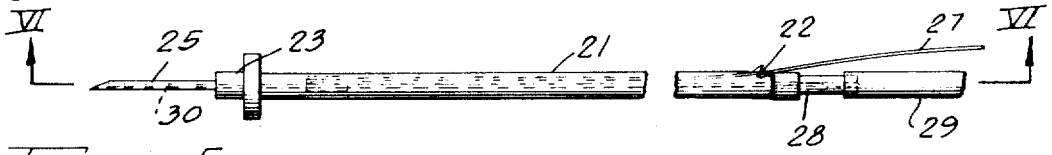
FIGURE 5 is a fragmentary side elevational view of another form of catheter placement unit embodying principles of this invention.
Figure 6:
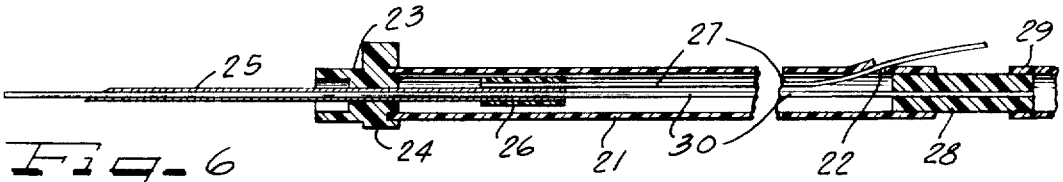
FIGURE 6 is a fragmentary enlarged vertical sectional view taken substantially as indicated by the line VI—VI of FIGURE 5.

In that embodiment of the invention seen in FIGURES 5 and 6, the needle is retracted after venipuncture by pulling on the end of a lanyard. With this form of the invention, it is impossible to advance the catheter beyond the point of the needle, and yet the venipuncture may be *tested* [teted] after the needle and catheter have been placed within a vein to the desired extent.

This form of the invention embodies a tubular sheath 21 of transparent plastic material, and which is imperforate except for a single small aperture 22. One end of this sheath is securely anchored to a flanged hub 23, one portion of the flange being flattened as indicated at 24 so that the structure will lie more closely against the body of a patient. A hollow needle 25 extends through the hub 23 and inside of the sheath 21 the [outer] *inner* end of the needle is circumscribed by a hub element 26 which securely locks one end of a lanyard 27 to the needle, this lanyard projecting out the aforesaid aperture 22 at the other end of the sheath.

The *other* [outer] end of the sheath 21 is secured to one end of a short tube 28, and the other end of the tube 28 is secured to a tube 29 leading from an infusion system. A catheter 30 is disposed within the sheath 21, having its outer end secured within the tube 28, and the other end of the catheter terminates within the needle 25 just inside the point of the needle.

*It should be noted that, to be operative, this embodiment must also be provided with means for holding the needle during venipuncture. This may be accomplished either as in the first embodiment, by use of gripping flanges (holding member 1) attached to the forward end of the sheath, or by making the sheath flexible so hub 26 can be gripped or pushed during venipuncture without contaminating the needle.*

With this structure, it is a simple expedient to connect the tube 29 to an infusion system, flush out the catheter with infusion liquid if so desired, then turn off infusion, and grasp the unit at or adjacent to the hub *26* [23] and make a proper venipuncture to the desired extent. When venipuncture is established, merely by pulling upon the lanyard the needle may be retracted relatively to the catheter until the point of the needle is inside the hub 23, and infusion again started. The device may be taped to the body of the patient as above described in connection with the first embodiment of the invention, and the lanyard may be knotted or a piece of adhesive tape secured thereto to prevent any unintentional movement of the needle relatively to the catheter.

Figure 7:
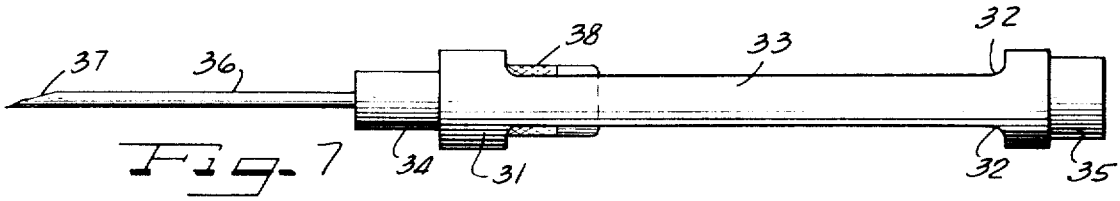
FIGURE 7 is a side elevational view of another form of catheter placement unit embodying principles of this invention.
Figure 8:
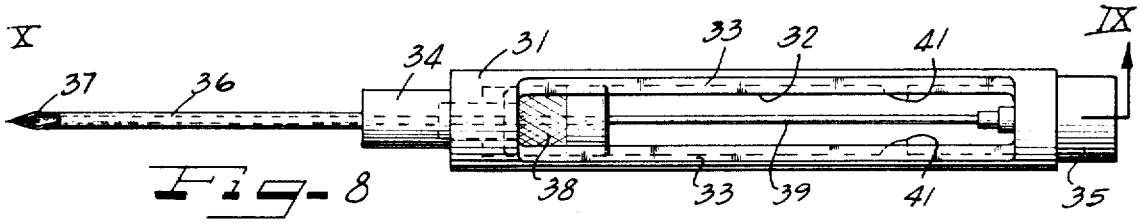
FIGURE 8 is a top plan view of the structure of FIGURE 7.
Figure 9:
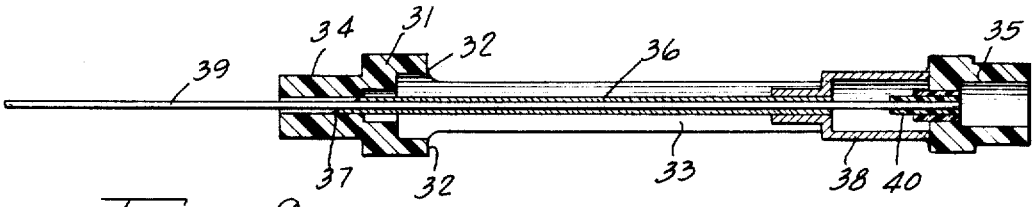
FIGURE 9 is a vertical sectional view of the structure of FIGURES 7 and 8 taken substantially as indicated by the line IX—IX of FIGURE 8, showing the structure after the catheter has been placed.

In that embodiment of the invention seen in FIGURES 7, 8 and 9, a plastic tube 31 is utilized, and this tube is provided with diametrically opposed and relatively large slots 32—32 therein so as to define a pair of opposed inwardly arcuate tracks 33—33. One end of this tube 31 is provided with a nipple 34 to receive the usual needle protective cap, not shown. The other end of the tube is provided with a nipple 35 for connection with an infusion system. A hollow needle 36 having a pointed end 37 projects through the nipple 34 when the placement unit is ready for use. The other end of the needle is firmly anchored in a cylindrical hub 38 slidable within the aforesaid tracks 33—33 from the position seen in FIGURES 7 and 8 with the needle hub abuting the end portion of the tube 31 to the position seen in FIGURE 9 with the needle hub abutting the opposite end portion of the tube 31.

A catheter 39 has the outer end thereof firmly anchored in a plug 40 in the outer end of the tube 31 so that communication through the nipple 35 is with the catheter only. The catheter extends through the tube 31 into the lumen of the needle 36 and terminates just inside the needle point 37. That portion of the catheter between the tracks 33—33 is not shielded, such not being necessary since only the part of the catheter within the lumen of the needle enters the patent's body.

The device of FIGURES 7, 8 and 9 may be used in similar manner to those previously described. In this instance, the placement unit may be removed from its sterile wrappings, connected to an infusion system, the catheter flushed out if desired, infusion stopped, and the hub 38 of the needle grasped between the thumb and finger of the attending surgeon. Venipuncture is then made to the desired extent, and it is a simple expedient to hold the tube 31 in position and retract the needle by sliding the hub 38 from the position seen in FIGURE 8 to the position seen in FIGURE 9, thus retracting the needle from the placed catheter. When the needle is fully retracted, the hub passes by a pair of detents 41—41 in the tracks 33—33, and the resiliency of the tracks permits the hub to pass between the detents which then fall into position back to the retracted hub and effectively lock it in that position against any advance movement relatively to the catheter. As seen in FIGURE 9, when the needle is fully retracted, the point 37 of the needle will be inside the nipple 34. And the patient is fully protected from the needle. The device may be adhesively attached to the body of the patient in the manner above described.

It will be understood that modification and variations may be effected without departing from the scope of the novel concepts of the present invention.

We claim as our invention:

1. In combination in a catheter placement unit, including tubular means, a hollow needle having a pointed end slidable in said means and initially disposed with the pointed end projecting out one end thereof, retracting means *on the other end of the needle* for retracting said needle back within said tubular means, [on the other end of said needle,]

a catheter extending through said tubular means with one end terminating just inside the pointed end of the needle, means [fixedly securing the other end of the catheter to the tubular means and] for connecting *the other end of said catheter* to an infusion system in a leakproof manner, *said connecting means being such that the needle can be retracted without retracting the catheter,* said tubular means [being in the form of] *including* a plastic conduit having an opening in the side wall thereof, and a part of said retracting means extending through said opening so that upon manipulation of said retracting means, said needle is retracted back within said tubular means thereby exposing said catheter.

2. *A* [In a] catheter placement unit as in claim 1 wherein said retracting means comprises a lanyard. [, a needle and a catheter assembly in which the needle and catheter are telescopically associated adjacent one end of the catheter, said catheter being in a sterile sheath, and means on the other end of the catheter for connection to an infusion system, wherein the improvement comprises said needle being slidably mounted in said sheath, a lanyard disposed in said sheath and connected to said needle to retract the same relatively to said catheter after entry of said catheter into a body lumen, the catheter being secured to said tubular means to connect the same to an infusion system and cannot be moved relatively to said needle.]

3. In combination in a catheter placement unit, including tubular means, a hollow needle having a pointed end *and being* slidable in said means and initially disposed with the pointed end projecting out one end thereof, retracting means *on the other end of said needle,* for retracting said needle back within said tubular means, [on the other end of said needle,]

a catheter [secured to and] extending through said tubular means with one end terminating just inside the pointed end of the needle, means to connect the other end of the catheter to an infusion system in a leakproof manner, *said connecting means being such that the needle can be retracted without retracting the catheter,* a flexible holder joined to the end of said tubular means from which the needle projects, means defining a groove in said holder in which said retracting means are initially disposed, and opposed wings on said holder which when bent upwardly and gripped together tighten said groove defining means on said retracting means to hold the needle firmly while a body puncture is made.

4. The combination of claim 3, including means to limit the retractive movement of the needle relatively to the catheter to a position wherein the pointed end of said needle rests in the groove of the holder.

5. In combination in a catheter placement unit, including tubular means, a hollow needle having a pointed end slidable in said means and initially disposed with the pointed end projecting out one end thereof, retracting means *on the other end of said needle,* for retracting said needle back within said tubular means [on the other end of said needle,]

a catheter extending through said tubular means with one end terminating just inside the pointed end of the needle, means to connect the other end of the catheter to an infusion system in a leakproof manner, *said connecting means being such that the needle can be retracted without retracting the catheter,* locking means carried by said tubular means to hold said needle in retracted position after placement of the catheter in a body lumen against advance movement relatively to the catheter, said retracting means comprising a grippable hub on said needle, a pair of opposed tracks defined by said tubular means between which said needle is slidable, and said locking means comprising an inwardly projecting detent on at least one of said tracks. [,]

[said tracks being sufficiently flexible for said hub to pass by said detent and lock therebehind.]

6. The combination of claim 5, including a hollow nipple on said tubular means having a bore of a size to just accommodate the needle and which extends well beyond the point of said needle when the needle is retracted to maintain the catheter in alignment with the lumen of the needle.

7. In a catheter placement unit having a needle and catheter assembly in which the needle and catheter are telescopically associated adjacent one end of the catheter, and means on the other end of the catheter for connection to an infusion system, *said connecting means being such that the needle can be retracted without retracting the catheter,* wherein the improvement comprises a flexible holder having a groove therein in which the needle end of said essembly is positioned, opposed wings on said holder which when bent upwardly and gripped together tighten the walls of said grove on said assembly to hold the same firmly while the needle and catheter are entered into a body lumen, and retracting means attached to said needle to retract the same relatively to the catheter when said wings are released after body entry.

*8. A combination as in claim 1, wherein the means for connecting the other end of the tubular means to an infusion system fixedly secures the other end of the catheter to the tubular means.*

*9. A combination as in claim 3, wherein the catheter is secured to the tubular means.*

*10. A combination as in claim 5, wherein the tracks are sufficiently flexible for the hub to pass by the detent and lock therebehind.*

*11. In combination in a catheter placement unit:*

*a tubular means,*

*a hollow needle having a pointed end and being slidable in the tubular means and initially disposed with the pointed end projecting out one end thereof,*

*grippable means fixedly secured to said needle for retracting said pointed end of the needle into the tubular means,*

*a catheter extending through the tubular means with one end therof within the needle,*

*means to connect the opposite end of said catheter to an infusion system in a leakproof manner, said connecting means being such that the needle can be rectracted without retracting the catheter,*

*said tubular means including a conduit having an opening in the side wall thereof, and*

*a part of said retracting means extending through said opening, so that, upon manipulation of said retracting means, said needle is retracted within said tubular means thereby exposing said catheter.*

*12. A combination as in claim 11, wherein there is additionally provided locking means carried by the tubular means to hold the needle in retracted position against advance movement relative to the tubular means after placement of the catheter in a body lumen.*

*13. In combination in a catheter placement unit:*

*tubular means,*

*a hollow needle having a pointed end and being slidable in the tubular means and initially disposed with the pointed end projecting out one end thereof,*

*flexible holding means encompassing the needle for manual gripping and tightening around the needle so said needle can be pushed to accomplish a venipuncture without retracting into the tubular means,*

*a lanyard secured to said needle and flexibly extending exteriorly of said tubular means so as to be pullable for retracting said pointed end of the needle into the tubular means but incapable of advancing the needle out of said tubular means,*

*a catheter extending through the tubular means with one end thereof within the needle, and*

*means to connect the opposite end of said catheter to an infusion system in a leakproof manner, said connecting means being such that the needle can be retracted without retracting the catheter.*

References Cited

The following references, cited by the Examiner, are of record in the patented file of this patent or the original patent.

UNITED STATES PATENTS

| | | | |
|---|---|---|---|
| 2,057,726 | 10/1936 | Landis | 128—214 R |
| 2,937,643 | 5/1960 | Elliot | 128—214.4 |
| 3,055,361 | 9/1962 | Ballard | 128—214.4 |
| 3,064,648 | 11/1962 | Bujan | 128—214 R |
| 3,262,449 | 7/1966 | Pannier et al. | 128—214.4 |
| 3,324,853 | 6/1967 | Czorny et al. | 128—214.4 |

DALTON L. TRULUCK, Primary Examiner

U.S. Cl. X.R.

128——221